(12) United States Patent
Yamashita

(10) Patent No.: US 8,216,588 B2
(45) Date of Patent: Jul. 10, 2012

(54) LYOPHILIZED PREPARATION COMPRISING INFLUENZA VACCINE, AND METHOD FOR PREPARATION THEREOF

(75) Inventor: Chikamasa Yamashita, Tokushima (JP)

(73) Assignee: Otsuka Pharmaceuticals Co., Ltd., Tokyo (JP)

( * ) Notice: Subject to any disclaimer, the term of this patent is extended or adjusted under 35 U.S.C. 154(b) by 171 days.

(21) Appl. No.: 12/529,893

(22) PCT Filed: Mar. 7, 2008

(86) PCT No.: PCT/JP2008/054210
§ 371 (c)(1),
(2), (4) Date: Sep. 3, 2009

(87) PCT Pub. No.: WO2008/111532
PCT Pub. Date: Sep. 18, 2008

(65) Prior Publication Data
US 2010/0104595 A1    Apr. 29, 2010

(30) Foreign Application Priority Data

Mar. 9, 2007 (JP) ................................ 2007-059724

(51) Int. Cl.
*A61K 39/145* (2006.01)
*A01N 25/02* (2006.01)
(52) U.S. Cl. ........................ 424/209.1; 424/93.1; 424/43
(58) Field of Classification Search ........................ None
See application file for complete search history.

(56) References Cited

U.S. PATENT DOCUMENTS

| | | | |
|---|---|---|---|
| 4,500,512 A | 2/1985 | Barme | |
| 4,537,769 A | 8/1985 | Cerini | |
| 7,282,219 B2 | 10/2007 | Nomura et al. | |
| 7,735,485 B2 * | 6/2010 | Yamashita et al. | 128/202.17 |
| 2004/0265987 A1 | 12/2004 | Trager et al. | |
| 2005/0037084 A1 | 2/2005 | Nomura et al. | |

FOREIGN PATENT DOCUMENTS

| | | | |
|---|---|---|---|
| JP | 58-183628 A | | 10/1983 |
| JP | 05-320071 A | | 12/1993 |
| JP | 06-065096 A | | 3/1994 |
| JP | WO2004/054555 | * | 7/2004 |
| JP | 2006-519028 A | | 8/2006 |
| WO | 2001/074397 A1 | | 10/2001 |
| WO | 2006/041819 A1 | | 4/2006 |

OTHER PUBLICATIONS

Miller G. J Exp. Med. 1944, pp. 507-520.*
Eckert E. Infection and Immunity, 1976, vol. 14, No. 6, pp. 1302-1308.*
Deborah A. Buonagurio, et al., "Genetic stability of live, cold-adapted influenza virus components of the FluMist/CAIV-T vaccine throughout the manufacturing process", Vaccine, 2006, pp. 2151-2160, vol. 24.
Stephen E. Zweig, "Advances in vaccine stability monitoring technology", Vaccine, 2006, pp. 5977-5985, vol. 24.
Robert J. Garmise, et al., "Formulation of a Dry Powder Influenza Vaccine for Nasal Delivery", AAPS PharmSciTech, 2006, pp. E1-E7, vol. 7(1), Article 19.
International Search Report of PCT/JP2008/054210 dated Jun. 17, 2008.
R.J. Cox et al., "Influenza Virus: Immunity and Vaccination Strategies. Comparison of the Immune Response to Inactivated and Live, Attenuated Influenza Vaccines", Scandinavian Journal of Immunology, 2004, 59: 1-15.
Russian Office Action issued Nov. 7, 2011 in corresponding RU Application No. 2009137380 (in the name of Otsuka Pharmaceutical Co., LTD., JP).
Israeli Patent Office, Notification of Defects issued in Israeli Patent Application No. 200588 dated Aug. 4, 2011.
J-P Amorij et al., "Development of Stable Influenza Vaccine Powder Formulations: Challenges and Possibilities", Pharm. Res., 2008, 25(6): 1256-1273 (Abstract).
J. Huang et al., "A novel dry powder influenza vaccine and intranasal delivery technology: induction of systemic and mucosal immune responses in rats", Vaccine, 2004, 23(6): 794-801 (Abstract).
Y.F. Maa et al., "Influenza vaccine powder formulation development: spray-freeze-drying and stability evaluation", J. Pharm. Sci., 2004, 93(7): 1912-1923 (Abstract).
Extended Search Report issued in EP Application No. 08721627.1 on Apr. 16, 2012, in the name of Otsuka Pharmaceutical Co., Ltd.
J-P. Amorij et al., "Pulmonary delivery of an inulin-stabilized influenza subunit vaccine prepared by spray-freeze drying induces systemic, mucosal humoral as well as cell-mediated immune responses in BALB/c mice", Vaccine, 2007, 25: 8707-8717.
J-P Amorij et al., "Rational design of an influenza subunit vaccine powder with sugar glass technology: Preventing conformational changes of haemagglutinin during freezing and freeze-drying", Vaccine, 2007, 25: 6447-6457.

* cited by examiner

*Primary Examiner* — Bao Li
(74) *Attorney, Agent, or Firm* — Sughrue Mion, PLLC

(57) ABSTRACT

The present invention aims to provide a freeze-dried preparation in which the influenza vaccine exhibits improved stability.
A freeze-dried preparation in which the influenza vaccine exhibits significantly improved stability can be obtained by freeze-drying an aqueous solution that meets the following conditions (A) to (C):
(A) (i) an influenza vaccine, (ii) a hydrophobic amino acid, and (iii) arginine and an acid addition salt thereof are incorporated;
(B) the proportion of the component (iii) is from 20 to 85% by weight relative to the total amount of the resulting freeze-dried preparation; and
(c) the pH is adjusted to be from 8 to 10 by controlling the proportion of arginine and an acid addition salt thereof that form the component (iii).

17 Claims, No Drawings

LYOPHILIZED PREPARATION COMPRISING INFLUENZA VACCINE, AND METHOD FOR PREPARATION THEREOF

TECHNICAL FIELD

The present invention relates to freeze-dried preparations containing an influenza vaccine. More particularly, the invention relates to a freeze-dried preparation in which the influenza vaccine exhibits improved stability. The present invention also relates to a method for producing the freeze-dried preparation.

BACKGROUND ART

Influenza is a disease caused by influenza viruses infecting the respiratory organs. In general, influenza causes a fever of 38° C. or higher in an individual infected with an influenza virus after a latency period of about 1 to 2 days, which is accompanied by general symptoms such as a headache, general malaise, and joint and muscle pains. Respiratory symptoms such as coughing and sputum follow, but the condition usually improves within a week. However, when influenza infects individuals such as the elderly, infants, expectant mothers, patients with chronic respiratory or circulatory system diseases, diabetics, or patients suffering from chronic kidney failure, serious and sometimes fatal complications such as pneumonia and bronchitis may develop. Moreover, influenza, which causes serious health problems, is also highly contagious, and numerous people become infected in a short period of time, resulting in enormous social and economical losses.

The administration of influenza vaccines is the most effective way to prevent health damage caused by influenza infections, and to reduce social and economical losses. Influenza vaccine preparations such as liquid preparations for use as injections and frozen preparations for use as nasal drops have been known in the past; however, no dry preparations of satisfactory stability have yet been made available to the market (see, for example, Non-Patent Document 1).

When influenza vaccines are distributed in the form of liquid preparations, they must always be maintained at low temperatures during distribution and preservation, in order to prevent the vaccines from becoming inactive; that is, cold chains are indispensable. Additionally, when influenza vaccines are distributed in the form of frozen preparations, it is necessary to maintain the vaccines in a frozen state during distribution and preservation in order to stably keep the preparations. The influenza vaccines that have been made into liquid or frozen preparations thus require advanced temperature control during transportation and preservation (see Non-Patent Document 2), making it difficult to distribute these preparations in areas with power supply shortages or without low-temperature transportation while maintaining the activity of the influenza vaccines.

In order to overcome such drawbacks of liquid or frozen preparations, it is effective to distribute influenza vaccines in the form of dry preparations. Although a technique concerning freeze-dried preparations of influenza vaccines has recently been proposed wherein influenza vaccines are made into preparations with the addition of lactose or trehalose, the stability of such preparations is nowhere indicated (see Non-Patent Document 3).

Like other vaccines, influenza vaccines are highly susceptible to heat, and are known to lose activity at high temperatures or below their freezing point (see Non-Patent Document 2). Even if the influenza vaccines are simply dried or freeze-dried, their activity problematically decreases with time during production or preservation. A technique to overcome this problem has yet to be found, and no successful examples of putting dry preparations of influenza vaccines into practical use have been reported to date.

Non-Patent Document 1: Deborah A. Buonagurio et al., *Vaccine*, vol. 24 (2006), 2151-2160
Non-Patent Document 2: Stephen E. Zweig, *Vaccine*, vol. 24 (2006), 5977-5985
Non-Patent Document 3: Robert J. Garmise et al., *AAPS PharmSciTech* 2006; 7 (1) Article 19, E1-E7

SUMMARY OF THE INVENTION

Problems to be Solved by the Invention

The present invention was made in view of the above-mentioned background techniques. An object of the present invention is to provide a freeze-dried preparation in which the influenza vaccine exhibits significantly improved stability.

Means for Solving the Problems

The present inventor conducted extensive research to overcome the aforementioned problems, and found that a freeze-dried preparation in which the influenza vaccine exhibits significantly improved stability can be obtained by freeze-drying an aqueous solution that meets the following conditions (A) to (C) in the production of a freeze-dried preparation containing an influenza vaccine:

(A) (i) an influenza vaccine, (ii) a hydrophobic amino acid, and (iii) arginine and an acid addition salt thereof are incorporated;

(B) the proportion of the component (iii) is from 20 to 85% by weight relative to the total amount of the resulting freeze-dried preparation; and (C) the pH is adjusted to from 8 to 10 by controlling the proportion of arginine to an acid addition salt thereof that form the component (iii).

The present invention has been accomplished by making further improvements based on these findings.

In summary, the present invention provides a freeze-dried preparation containing an influenza vaccine as set forth below.

Item 1. A freeze-dried preparation containing an influenza vaccine, obtained by freeze-drying an aqueous solution comprising (i) an influenza vaccine, (ii) a hydrophobic amino acid, and (iii) arginine and an acid addition salt thereof; the proportion of the component (iii) relative to the total amount of the freeze-dried preparation being from 20 to 85% by weight; and the proportion of the arginine to the acid addition salt thereof being in a range such that the pH of the aqueous solution is from 8 to 10.

Item 2. A freeze-dried preparation according to Item 1, wherein the influenza vaccine is subjected to a desalting process.

Item 3. A freeze-dried preparation according to Item 1, wherein the (ii) hydrophobic amino acid is phenylalanine, or a combination of phenylalanine with at least one of valine, leucine, and isoleucine.

Item 4. A freeze-dried preparation according to Item 1, wherein the proportion of the (ii) hydrophobic amino acid is from 14 to 75% by weight relative to the total amount of the freeze-dried preparation.

Item 5. A freeze-dried preparation according to Item 1, wherein the (iii) arginine and the acid addition salt thereof is arginine and a hydrochloride thereof, respectively.

Item 6. A freeze-dried preparation according to Item 1, wherein the proportion of the acid addition salt of arginine is 1 to 20 parts by weight relative to 1 part by weight of the arginine.

Item 7. A freeze-dried preparation according to Item 1, wherein the total amount of the components (i) to (iii) is from 80 to 100% by weight relative to the total amount of the freeze-dried preparation.

Item 8. A freeze-dried preparation according to Item 1, which is an injection that is dissolved prior to use.

Item 9. A freeze-dried preparation according to Item 1, which is a pharmaceutical preparation for transpulmonary administration.

Item 10. A freeze-dried preparation according to Item 1, which is a pharmaceutical preparation for nasally administration.

Moreover, the present invention also provides a method for producing a freeze-dried preparation containing an influenza vaccine, as set forth below.

Item 11. A method for preparing a freeze-dried preparation containing an influenza vaccine, comprising:

a first step of preparing an aqueous solution comprising (i) an influenza vaccine, (ii) a hydrophobic amino acid, and (iii) arginine and an acid addition salt thereof; the content of the (i) influenza vaccine in the aqueous solution being equivalent to 20 to 80% by weight relative to the total amount of the resulting freeze-dried preparation; and the pH of the aqueous solution being from 8 to 10; and a second step of freeze-drying the resulting aqueous solution.

Item 12. A method according to Item 11, wherein the (i) influenza vaccine is subjected to a desalting process.

Item 13. A method according to Item 11, wherein the (ii) hydrophobic amino acid is phenylalanine, or a combination of phenylalanine with at least one of valine, leucine, and isoleucine.

Item 14. A method according to Item 11, wherein the content of the (ii) hydrophobic amino acid in the aqueous solution used in the first step is equivalent to 14 to 75% by weight relative to the total amount of the resulting freeze-dried preparation.

Item 15. A method according to Item 11, wherein the (iii) arginine and the acid addition salt thereof is arginine and a hydrochloride thereof, respectively.

Item 16. A method according to Item 11, wherein the proportion of the acid addition salt of arginine in the aqueous solution used in the first step is 1 to 20 parts by weight relative to 1 part by weight of the arginine.

Item 17. A method according to Item 11, wherein the total content of the components (i) to (iii) in the aqueous solution used in the first step is equivalent to 80 to 100% by weight relative to the total amount of the resulting freeze-dried preparation.

Effects of the Invention

The freeze-dried preparation of the invention can stably maintain the activity of an influenza vaccine during preservation, thus making it easier to distribute and preserve, compared with previous preparations.

Moreover, the freeze-dried preparation can be used as an injection by dissolving it in an injection solution prior to use, or as a preparation for transpulmonary administration or a nasally administration as it is; hence, another advantage of the freeze-dried preparation is that it can be applied to various methods of administration.

DESCRIPTION OF PREFERRED EMBODIMENTS

In the specification, the pH denotes a value measured at 25° C.

A freeze-dried preparation of the invention comprises (i) an influenza vaccine, (ii) a hydrophobic amino acid, and (iii) arginine and an acid addition salt thereof; wherein a specific proportion of the component (iii) is incorporated, and the proportion of the arginine to the acid addition salt thereof forming the component (iii) satisfies a specific range.

Influenza vaccines suitable as the influenza vaccine used in the freeze-dried preparation of the invention (hereinafter sometimes denoted simply as the "component (i)") include sub-unit vaccines produced after the purification of viral particles grown in embryonated chicken eggs and influenza HA (hemagglutinin) vaccines, which are one type of split vaccine. Influenza vaccines derived from tissue cultures may also be used. Alternatively, live vaccines produced from attenuated influenza viruses, component vaccines produced from detoxified influenza viruses with their immunogenicity intact, or whole viral particles produced from inactivated whole viral particles may also be used. The influenza vaccine for use in the present invention may be produced from either or both of the A and B strains, but is suitably produced from the influenza vaccines of both the A and B strains.

An influenza vaccine produced according to a known method or a commercially available influenza vaccine may be used as the influenza vaccine for use in the invention.

When the produced influenza vaccine or a commercially available influenza vaccine is in the form of a solution or a powder and contains a salt such as a buffer or a preservative, the influenza vaccine is desirably subjected to a preliminary desalting process to remove the salt. When the influenza vaccine is thus subjected to a preliminary desalting process, the stability of the influenza vaccine in the freeze-dried preparation of the invention can be enhanced more effectively. The method of desalting the influenza vaccine is not particularly limited, and examples include ultrafiltration, sedimentation, ion exchange, dialysis, and the like. In order to prevent the activity of the influenza vaccine from decreasing during the desalting process, desalting is desirably carried out using an aqueous solution whose pH is adjusted to be from 8 to 10, and preferably from 8 to 9, with an alkaline substance such as sodium hydroxide, potassium hydroxide, arginine, or the like. In particular, a solution with the same composition as that of the solution subjected to freeze-drying in the production of the freeze-dried preparation of the invention, except that the influenza vaccine is not included, is suitable as the solution for use in the desalting process.

The proportion of the component (i) used in the freeze-dried preparation of the invention may be suitably determined according to the method of applying the freeze-dried preparation and the like. For example, the proportion of the component (i) relative to the total amount of the freeze-dried preparation is from 0.3 to 60% by weight, preferably 1 to 50% by weight, more preferably 2 to 40% by weight, still more preferably 3 to 30% by weight, and particularly preferably 3 to 20% by weight.

Specific examples of the hydrophobic amino acid contained in the freeze-dried preparation of the invention (hereinafter sometimes denoted simply as the "component (ii)") include protein-composing amino acids such as valine, leucine, isoleucine, phenylalanine, and the like. In the invention, these hydrophobic amino acids may be used singly or in combination. In the invention, for example, phenylalanine alone or a combination of phenylalanine with at least one of valine, leucine, and isoleucine may preferably be used as the hydrophobic amino acids.

The proportion of the component (ii) used in the freeze-dried preparation of the invention may be suitably determined according to the type of the component (ii), the method of applying the freeze-dried preparation, and the like. For example, the proportion of the component (ii) relative to the total amount of the freeze-dried preparation is 14 to 75% by weight, preferably 20 to 75% by weight, more preferably 20 to 70% by weight, still more preferably 25 to 65% by weight, and particularly preferably 30 to 60% by weight.

The freeze-dried preparation of the invention further comprises arginine and an acid addition salt thereof (hereinafter sometimes denoted simply as the "component (iii)"). That is to say, the freeze-dried preparation essentially comprises a combination of arginine and an acid addition salt thereof.

The acid addition salt of arginine for use in the invention is not particularly limited as long as it is pharmacologically acceptable, and examples include inorganic acid addition salts such as hydrochlorides, nitrates, and sulfates; and organic acid addition salts such as acetates. Arginine hydrochloride is mentioned as a preferable example of the arginine acid addition salt for use in the invention. In the invention, an arginine acid addition salt may be used alone or two or more arginine acid addition salts may be used in combination.

In the freeze-dried preparation of the invention, a total amount of the component (iii) (i.e., the total amount of the arginine and the acid addition salt thereof) is incorporated in a proportion of 20 to 85% by weight relative to the total amount of the freeze-dried preparation. Such a proportion of the component (iii) prevents a decrease in the activity of the influenza vaccine during preservation, thereby providing a preparation with excellent stability. The proportion of the component (iii) relative to the total amount of the freeze-dried preparation is preferably 20 to 80% by weight, more preferably 20 to 75% by weight, still more preferably 25 to 70% by weight, and particularly preferably 30 to 65% by weight.

The component (iii) satisfies any of these proportions, and is also such that the proportion of the arginine to the acid addition salt thereof is adjusted so that the pH of the aqueous solution subjected to freeze-drying is from 8 to 10. That is to say, arginine is alkaline, and an acid addition salt of arginine is acidic, so that the pH of the aqueous solution subjected to freeze-drying is adjusted within that range by adjusting the proportion of the arginine to the arginine acid addition salt, provided that the amount of the component (iii) used satisfying any of the aforementioned ranges. By thus adjusting the pH of the aqueous solution subjected to freeze-drying within the aforementioned range using arginine and an acid addition salt thereof, it is possible to enhance the preservation stability of the influenza vaccine. More preferably, the proportion of the arginine to the acid addition salt thereof is adjusted so that the pH of the aqueous solution subjected to freeze-drying is from 8 to 9. The term "aqueous solution subjected to freeze-drying" as referred to herein means an aqueous solution subjected to freeze-drying in the production of the freeze-dried preparation, i.e., an aqueous solution obtained by adding all of the components of the freeze-dried preparation of the invention to purified water. The aqueous solution subjected to freeze-drying is adjusted so that, for example, the total amount of the freeze-dried preparation (the total amount of all the components) per 1 mL of the aqueous solution is 0.2 to 20 mg, preferably 0.4 to 20 mg, more preferably 0.4 to 15 mg, still more preferably 0.6 to 12.5 mg, particularly preferably 1 to 10 mg, although the invention is not particularly limited to these amounts.

The proportion of arginine to an acid addition salt thereof in the component (iii) is not particularly limited as long as the pH of the aqueous solution subjected to freeze-drying can be within the aforementioned range, and is suitably determined according to the type of the acid addition salt, the type of the component (ii) used, and the like. Specifically, the proportion of an arginine acid addition salt relative to 1 part by weight of arginine may, for example, be 1 to 20 parts by weight, preferably 1 to 15 parts by weight, more preferably 1.25 to 12.5 parts by weight, still more preferably 1.5 to 12.5 parts by weight, and particularly preferably 2 to 10 parts by weight.

The freeze-dried preparation of the invention may comprise, in addition to the components (i) to (iii), hydrophilic amino acids other than arginine (hereinafter sometimes denoted simply as the "component (iv)") in such a range that the effects of the invention are not impaired. The hydrophilic amino acid may be any amino acid with a hydrophilic side chain, regardless of whether it is a protein-composing amino acid or not. Specific examples of hydrophilic amino acids include basic amino acids such as lysine, histidine, and the like; neutral hydroxyamino acids such as serine, threonine, and the like; acidic amino acids such as aspartic acid, glutamic acid, and the like; amide group-containing amino acids such as asparagine, glutamine, and the like; glycine, alanine, cysteine, tyrosine, and other amino acids. Preferable among these hydrophilic amino acids are alanine and glycine. Such a hydrophilic amino acid may be used singly, or two or more of them may be used in combination.

When such a hydrophilic amino acid is contained in the freeze-dried preparation of the invention, the proportion of the hydrophilic amino acid is not also particularly limited; but, for example, the proportion of the hydrophilic amino acid relative to the total amount of the freeze-dried preparation may be 5 to 50% by weight, preferably 5 to 40% by weight, more preferably 5 to 30% by weight, still more preferably 5 to 25% by weight, and particularly preferably 10 to 25% by weight.

Moreover, in order to make the effect of stabilizing the influenza vaccine more significant in the freeze-dried preparation of the invention, the total amount of the components (i) to (iii) where the component (iv) is not included, or the total amount of the components (i) to (iv) where the component (iv) is included, is 80 to 100% by weight, preferably 85 to 100% by weight, more preferably 90 to 100% by weight, still more preferably 95 to 100% by weight, and particularly preferably 100% by weight, relative to the total amount of the freeze-dried preparation.

The freeze-dried preparation of the invention may also comprise the following components as long as the effects of the invention are not impaired: monosaccharides such as glucose; disaccharides such as sucrose, maltose, lactose, and trehalose; sugar alcohols such as mannitol; oligosaccharides such as cyclodextrin; polysaccharides such as dextran 40 and pullulan; polyhydric alcohols such as polyethylene glycol; fatty acid salts such as sodium caprate; human serum albumin; inorganic salts; gelatin; surfactants; buffers; and so forth. The surfactant may either be anionic, cationic, or nonionic, as long as it is a surfactant usually used in pharmaceutical products. Additionally, the freeze-dried preparation of the present invention optionally contains an adjuvant.

The freeze-dried preparation of the invention is produced by adding predetermined amounts of the components (i) to (iii) to purified water, adding the component (iv) and other components as necessary, and subjecting the mixture to a freeze-drying process. More specifically, the freeze-dried preparation of the invention can be produced through the following first and second steps:

the first step: preparing an aqueous solution comprising (i) an influenza vaccine, (ii) a hydrophobic amino acid, and (iii) arginine and an acid addition salt thereof, wherein the amount of the (iii) arginine and the acid addition salt thereof is equivalent to 20 to 85% by weight relative to the total amount of the resulting freeze-dried preparation, and the pH is from 8 to 10; and the second step: freeze-drying the aqueous solution prepared in the first step to obtain a freeze-dried preparation.

The target freeze-dried preparation can be obtained by subjecting the aqueous solution prepared in the first step to a freeze-drying process. Therefore, in the first step, the aqueous solution subjected to freeze-drying is prepared so that the proportion of the components in the aqueous solution other than the component(s) removed by freeze-drying is the same as the proportion of the components in the resulting preparation. Moreover, the pH of the aqueous solution prepared in the first step is adjusted by controlling the proportion of the arginine to the acid addition salt of arginine, as described above.

The freeze-dried preparation of the invention may be a dried solid (freeze-dried cake) itself obtained by a freeze-drying process, or may be a powder produced from the dried solid.

The method of administration of the freeze-dried preparation of the invention is not particularly limited. For example, the preparation may be dissolved in a diluent (injection solution) prior to use and subcutaneously administered as an injection. The freeze-dried preparation may also be dissolved in a diluent to form a liquid preparation, and transpulmonarily or intranasally administered as a pharmaceutical preparation for transpulmonary administration or nasal drop administration. Moreover, the freeze-dried preparation can be made into a powder by applying an air impact; therefore, when the freeze-dried preparation is used as a pharmaceutical preparation for transpulmonary administration or nasal drop administration, it can be transpulmonarily or intranasally administered as it is, using a dry powder inhalation device in which the air impact can be applied.

The method of administering the freeze-dried preparation is suitably determined depending on the age and the like of the subject, but the preparation may be administered, for example, in an amount equivalent to 3 to 300 µg of the influenza vaccine, once or twice at an interval of about 1 to 4 weeks.

When the freeze-dried preparation is administered as it is without being dissolved in a diluent prior to use, it is preferably housed in a container for each single dose (the amount administered at one time) in view of the convenience of use. When the freeze-dried preparation is administered by dissolution in a diluent prior to use, it may be housed in a container for each single dose, or multiple doses of the preparation may be housed together in a container.

The freeze-dried preparation contains a reduced amount of excipient compared to preparations containing influenza vaccines that have previously been used as injections. Therefore, one feature of the preparation is that the amount of the preparation per container is small. In the present invention, the amount of the freeze-dried preparation housed in a container is not particularly limited, but is, for example, 0.1 to 10 mg, preferably 0.15 to 8 mg, more preferably 0.2 to 6 mg, still more preferably 0.25 to 5 mg, and particularly preferably 0.3 to 5 mg.

EXAMPLES

The present invention will be described in more detail below with reference to Examples and the like, which are not intended to limit the invention.

Reference Example 1

Study of Desalting Conditions for Influenza Vaccines

Conditions of the desalting process for influenza HA vaccine solutions were studied. Specifically, an influenza HA vaccine "Seiken" (product name, manufactured by Denka Seiken, Lot No. 308-A) was used as an influenza HA vaccine solution, and a suitable amount of this solution was poured into each Vivaspin 4 mL concentrator (manufactured by Sartorius) and centrifuged at 3000 rpm for 30 minutes. Each one of the solutions of the formulations shown in Table 1 was then added to each Vivaspin concentrator, and the mixtures were centrifuged at 3000 rpm for 30 minutes. This procedure was repeated a total of three times.

The resulting desalted influenza HA vaccines were measured for their activity (HA value) in accordance with the method described below.

Measurement of Activities of Influenza HA Vaccines

1. Preparation of 5 vol % Chicken Erythrocyte Suspension

Preserved chicken blood (by Nippon Biotest Labo.) was placed in a test tube and centrifuged for 5 minutes at 900 g, followed by the removal of the supernatant and the leucocyte layer. A diluent of the composition shown below (a 1/200 mol/L phosphate-buffered sodium chloride solution (pH 7.2)) was then added to the erythrocytes in the test tube. The mixture was stirred and subsequently centrifuged to remove the supernatant. The procedure was repeated three times. The erythrocytes in the test tube were drawn with a pipet and placed in a container containing the diluent, and were mixed to prepare a 5 vol % chicken erythrocyte suspension.

| Diluent Composition | |
|---|---|
| NaCl | 8.5 g |
| $Na_2HPO_4 \cdot 12H_2O$ | 1.425 g |
| $KH_2PO_4$ | 0.135 g |
| Purified water | 1000 mL |

2. Measurement of HA Values

Each of 50 µL portion of the influenza HA vaccine solutions with different dilution factors was added to a microplate, and then 50 µL of the 0.5 vol % chicken erythrocyte suspension was added thereto (a two-stage dilution method). The samples in the microplate were mixed well and left standing at room temperature for an hour, and then the highest dilution factor among the samples of each influenza HA vaccine with the erythrocytes being completely agglutinated was evaluated as its HA value.

The results are shown in Table 1. The results confirmed that the influenza HA vaccines subjected to a desalting process with a solution of pH 7 or below undergo decreases in activity; however, the influenza HA vaccines subjected to a desalting process with a solution of pH 8 to 9 are capable of retaining stable activity.

TABLE 1

|  | Formulations and pHs of the Solutions | Residual Activity |
|---|---|---|
| Condition 1 | 0.5 mg of Phe added into 0.5 mL of purified water; the pH adjusted to 3.0 with NaOH | 12.5% |
| Condition 2 | 0.5 mg of Phe added into 0.5 mL of purified water; the pH adjusted to 4.0 with NaOH | 6.3% |
| Condition 3 | 0.5 mg of Phe added into 0.5 mL of purified water; the pH adjusted to 5.7 with NaOH | 12.5% |
| Condition 4 | 0.5 mg of Phe added into 0.5 mL of purified water; the pH adjusted to 7.0 with NaOH | 50% |
| Condition 5 | No Phe added into 0.5 mL of purified water; the pH adjusted to 7.0 with NaOH | 50% |
| Condition 6 | 0.5 mg of Phe added into 0.5 mL of purified water; the pH adjusted to 8.0 with NaOH | 100% |
| Condition 7 | No Phe added into 0.5 mL of purified water; the pH adjusted to 8.0 with NaOH | 100% |
| Condition 8 | 0.5 mg of Phe added into 0.5 mL of purified water; the pH adjusted to 9.0 with NaOH | 100% |

The "residual activity" in Table 1 denotes the proportion (%) of the HA value after the desalting process relative to the HA value before the desalting process.

Test Example 1

Evaluation of the Stabilities of Influenza Vaccines

An influenza HA vaccine "Seiken" (product name, manufactured by Denka Seiken, Lot No. 308-A) was used as an influenza HA vaccine solution, and 1 mL (equivalent to 90 of the influenza HA vaccine) of this solution was poured into each Vivaspin 4 mL concentrator (manufactured by Sartorius) and centrifuged at 3000 rpm for 30 minutes. Each one of the solutions of the compositions shown in Table 2 was then added into each Vivaspin concentrator, and the mixtures were centrifuged at 3000 rpm for 30 minutes. This procedure was repeated a total of three times. The final solutions obtained after such concentration and desalting (buffer exchange) had the compositions shown in Table 2, and their volume was adjusted to the initial volume (1 mL). A glass vial was filled with 0.5 mL of each of the prepared solutions, and the solutions were freeze-dried to give freeze-dried products.

TABLE 2

|  | Formulations and pHs of the Solutions Used in the Examples and Comparative Examples |
|---|---|
| Example 1 | 0.5 mg of Phe, 0.5 mg of Arg-HCl and 0.075 mg of Arg added into 0.5 mL of purified water; pH 8 |
| Example 2 | 0.5 mg of Phe, 0.3 mg of Arg-HCl and 0.050 mg of Arg added into 0.5 mL of purified water; pH 8 |
| Example 3 | 0.5 mg of Phe, 0.2 mg of Ile, 0.3 mg of Arg-HCl and 0.057 mg of Arg added into 0.5 mL of purified water; pH 8 |
| Example 4 | 0.5 mg of Phe, 0.2 mg of Val, 0.3 mg of Arg-HCl and 0.055 mg of Arg added into 0.5 mL of purified water; pH 8 |
| Example 5 | 0.5 mg of Phe, 0.2 mg of Leu, 0.3 mg of Arg-HCl and 0.052 mg of Arg added into 0.5 mL of purified water; pH 8 |
| Example 6 | 0.5 mg of Phe, 0.2 mg of Ala, 0.3 mg of Arg-HCl and 0.052 mg of Arg added into 0.5 mL of purified water; pH 8 |
| Example 7 | 0.5 mg of Phe, 0.2 mg of Gly, 0.3 mg of Arg-HCl and 0.052 mg of Arg added into 0.5 mL of purified water; pH 8 |
| Comparative Example 1 | 0.5 mg of Phe and a suitable amount of NaOH added into 0.5 mL of purified water; pH 8 |
| Comparative Example 2 | 0.5 mg of Phe and 0.060 mg of Arg added into 0.5 mL of purified water; pH 8 |
| Comparative Example 3 | 0.5 mg of Arg-HCl and 0.030 mg of Arg added into 0.5 mL of purified water; pH 8 |
| Comparative Example 4 | 0.5 mg of Phe, 0.5 mg of His and 0.030 mg of Arg added into 0.5 mL of purified water; pH 8 |

The pH of the solutions used in Examples 1 to 7 and Comparative Examples 2 to 4 was adjusted to 8 using predetermined amounts of their components without the use of other pH adjusters. NaOH was added to the solution used in Comparative Example 1 so that the pH was 8 after the addition of a predetermined amount of its component.

The resulting freeze-dried preparations were encapsulated in each glass vial and preserved for 4 weeks in a dark place at 25° C./60% RH. Immediately after preparation and 1, 2, 3, and 4 weeks after preservation, the influenza HA vaccine in each freeze-dried preparation was measured for its HA value according to the same method as described in Reference Example 1.

The results are shown in Table 3. In the cases of using the solutions containing phenylalanine whose pH was adjusted to 8 with only sodium hydroxide and arginine, it was impossible to prevent the activity of the influenza HA vaccines from decreasing during preservation (Comparative Examples 1 and 2). Also in the case of using the solution whose pH was adjusted to 8 via the addition of arginine and arginine hydrochloride without the addition of phenylalanine, which is a hydrophobic amino acid, it was impossible to prevent the activity of the influenza HA vaccine from decreasing (Comparative Example 3). Moreover, in the case of using the solution whose pH was adjusted to 8 using a combination of phenylalanine, histidine, which is a basic amino acid, and arginine, it was impossible to prevent the activity of the influenza HA vaccine from decreasing.

On the contrary, it was found that when the solution for use in the preparation of a freeze-dried preparation meets the conditions (1) to (3) set forth below, the activity of the influenza HA vaccine in the final freeze-dried preparation can be stably maintained: (1) a hydrophobic amino acid, arginine, and an arginine acid addition salt are incorporated; (2) the proportion of the arginine to the arginine acid addition salt is adjusted so that the pH of the solution is 8; (3) the total amount of the arginine and arginine acid addition salt is adjusted to equal to or higher than a predetermined concentration in the freeze-dried preparation.

TABLE 3

|  |  | Residual Activity | | | |
|---|---|---|---|---|---|
|  | Formulations of the Freeze-Dried Preparations | Immediately After Preparation | After 1 week | After 2 weeks | After 4 weeks |
| Example 1 | 4.0% HA vaccine, 44.6% Phe, 51.4% Arg and Arg-HCl | 100% | 100% | 100% | 100% |
| Example 2 | 5.0% HA vaccine, 55.9% Phe, 39.1% Arg and Arg-HCl | 100% | — | 100% | — |
| Example 3 | 4.1% HA vaccine, 45.4% Phe, 18.1% Ile, 32.4% Arg and Arg-HCl | 100% | — | 100% | — |
| Example 4 | 4.1% HA vaccine, 45.4% Phe, 18.2% Val, 32.3% Arg and Arg-HCl | 100% | — | 100% | — |

TABLE 3-continued

| Formulations of the Freeze-Dried Preparations | Residual Activity | | | |
| --- | --- | --- | --- | --- |
| | Immediately After Preparation | After 1 week | After 2 weeks | After 4 weeks |
| Example 5: 4.1% HA vaccine, 45.6% Phe, 18.2% Leu, 32.1% Arg and Arg-HCl | 100% | — | 100% | — |
| Example 6: 4.1% HA vaccine, 45.6% Phe, 18.2% Ala, 32.1% Arg and Arg-HCl | 100% | — | 100% | — |
| Example 7: 4.1% HA vaccine, 45.6% Phe, 18.2% Gly, 32.1% Arg and Arg-HCl | 100% | — | 100% | — |
| Comparative Example 1: About 8.3% HA vaccine, about 91.7% Phe, a suitable amount of NaOH | 100% | 25% | 6.3% | 3.1% |
| Comparative Example 2: 7.4% HA vaccine, 82.7% Phe, 9.9% Arg | 100% | 50% | 25% | 25% |
| Comparative Example 3: 7.8% HA vaccine, 92.2% Arg and Arg-HCl | 100% | — | 25% | — |
| Comparative Example 4: 4.2% HA vaccine, 46.5% Phe, 46.5% His, 2.8% Arg | 100% | 50% | 12.5% | 6.3% |

The "residual activity" in Table 3 denotes the proportion (%) of the HA value of the freeze-dried preparation after preservation relative to the HA value of the freeze-dried preparation immediately after the preparation.
In Table 3, the unit % in the "Compositions of the Freeze-Dried Formulations" column denotes % by weight.
In Table 3, "—" denotes "not measured".

The invention claimed is:

1. A freeze-dried preparation containing an influenza vaccine, obtained by freeze-drying an aqueous solution comprising (i) an influenza vaccine, (ii) a hydrophobic amino acid, and (iii) arginine and an acid addition salt thereof;
the proportion of the (iii) arginine and the acid addition salt thereof relative to the total amount of the freeze-dried preparation being from 20 to 85% by weight; and the proportion of the arginine to the acid addition salt thereof being in a range such that the pH of the aqueous solution is from 8 to 10.

2. A freeze-dried preparation according to claim 1, wherein the influenza vaccine is subjected to a desalting process.

3. A freeze-dried preparation according to claim 1, wherein the (ii) hydrophobic amino acid is phenylalanine, or a combination of phenylalanine with at least one of valine, leucine, and isoleucine.

4. A freeze-dried preparation according to claim 1, wherein the proportion of the (ii) hydrophobic amino acid is from 14 to 75% by weight relative to the total amount of the freeze-dried preparation.

5. A freeze-dried preparation according to claim 1, wherein the (iii) arginine and the acid addition salt thereof is arginine and a hydrochloride thereof, respectively.

6. A freeze-dried preparation according to claim 1, wherein the proportion of the acid addition salt of arginine is 1 to 20 parts by weight relative to 1 part by weight of the arginine.

7. A freeze-dried preparation according to claim 1, wherein the total amount of the components (i) (ii) and (iii) is from 80 to 100% by weight relative to the total amount of the freeze-dried preparation.

8. A freeze-dried preparation according to claim 1, which is an injection that is dissolved prior to use.

9. A freeze-dried preparation according to claim 1, which is a pharmaceutical preparation for transpulmonary administration.

10. A freeze-dried preparation according to claim 1, which is a pharmaceutical preparation for nasally administration.

11. A method for preparing a freeze-dried preparation containing an influenza vaccine, comprising:
a first step of preparing an aqueous solution comprising (i) an influenza vaccine, (ii) a hydrophobic amino acid, and (iii) arginine and an acid addition salt thereof; the content of the (iii) arginine and the acid addition salt thereof in the aqueous solution being equivalent to 20 to 85% by weight relative to the total amount of the resulting freeze-dried preparation; and the pH of the aqueous solution being from 8 to 10; and
a second step of freeze-drying the resulting aqueous solution.

12. A method according to claim 11, wherein the influenza vaccine is subjected to a desalting process.

13. A method according to claim 11, wherein the (ii) hydrophobic amino acid is phenylalanine, or a combination of phenylalanine with at least one of valine, leucine, and isoleucine.

14. A method according to claim 11, wherein the content of the (ii) hydrophobic amino acid in the aqueous solution used in the first step is equivalent to 14 to 75% by weight relative to the total amount of the resulting freeze-dried preparation.

15. A method according to claim 11, wherein the (iii) arginine and the acid addition salt thereof is arginine and a hydrochloride thereof, respectively.

16. A method according to claim 11, wherein the proportion of the acid addition salt of arginine in the aqueous solution used in the first step is 1 to 20 parts by weight relative to 1 part by weight of the arginine.

17. A method according to claim 11, wherein the total content of the components (i) (ii) and (iii) in the aqueous solution used in the first step is equivalent to 80 to 100% by weight relative to the total amount of the resulting freeze-dried preparation.

* * * * *